(12) United States Patent  (10) Patent No.: US 11,064,758 B2
Dervish et al.  (45) Date of Patent: Jul. 20, 2021

(54) SOLE OR INNER SOLE

(71) Applicant: IMPACT TECH LABS AG, Zurich (CH)

(72) Inventors: Kemal Dervish, Welwyn Garden City (GB); Haim Geva, London (GB); Jason Lloyd Roberts, St. Margarets (GB); Giles Tongue, West Byfleet (GB); Grant Trewartha, Wiltshire (GB)

(73) Assignee: NURVV LIMITED, Twickenham (GB)

( * ) Notice: Subject to any disclaimer, the term of this patent is extended or adjusted under 35 U.S.C. 154(b) by 0 days.

(21) Appl. No.: 16/022,096

(22) Filed: Jun. 28, 2018

(65) Prior Publication Data

US 2019/0000177 A1  Jan. 3, 2019

(30) Foreign Application Priority Data

Jun. 29, 2017 (GB) ..................................... 1710445

(51) Int. Cl.
*A43B 3/00* (2006.01)
*A43B 13/00* (2006.01)
(Continued)

(52) U.S. Cl.
CPC ............ *A43B 3/0005* (2013.01); *A43B 7/142* (2013.01); *A43B 7/144* (2013.01); *A43B 7/145* (2013.01);
(Continued)

(58) Field of Classification Search
CPC ..... A43B 3/0005; A43B 7/142; A43B 7/1425; A43B 7/1435; A43B 7/144; A43B 7/145;
(Continued)

(56) References Cited

U.S. PATENT DOCUMENTS 4,745,930 A * 5/1988 Confer ................. A43B 3/0005
600/592
5,929,332 A * 7/1999 Brown ..................... A43B 3/00
36/136
(Continued)

FOREIGN PATENT DOCUMENTS

DE  10201134 A1  7/2003
DE  102012004117 A1  9/2013
WO  2017/033036 A1  3/2017

OTHER PUBLICATIONS

Intellectual Property Office (the United Kingdom), Search Report issued in corresponding Application No. GB1710445.6, dated Nov. 30, 2017.

*Primary Examiner* — Timothy K Trieu
*Assistant Examiner* — Dakota Marin
(74) *Attorney, Agent, or Firm* — Stites & Harbison, PLLC; Jeffrey A. Haeberlin; Gary N. Stewart

(57) ABSTRACT

A sole (100) or inner sole for a shoe is provided. The sole (100) or inner sole comprises: a toe region (28) for supporting a user's toes; a forefoot region (26) for supporting a user's forefoot; a midfoot region (24) for supporting a user's arch; and a heel region (22) for supporting a user's heel. A longitudinal direction (X) extends from the heel region (22) towards the toe region (28). A lateral direction (Y) transverse to the longitudinal direction (X) extends from an inner side to an outer side of the sole (100) or inner sole. A plurality of force sensors (10) distributed throughout the sole (100) or inner sole. The plurality of force sensors (10) comprise: a first lateral row of force sensors (10) in the toe region (28); a second lateral row of force sensors (10) in the forefoot region (26); a first longitudinal row of force sensors (10) along the inner side of the sole (100) or inner sole from the heel region (22) to the midfoot region (24); and a second longitudinal row of force sensors (10) along the outer side of (Continued)

the sole (100) or inner sole from the heel region (22) to the midfoot region (24).

9 Claims, 5 Drawing Sheets

(51) Int. Cl.
*A61B 5/103* (2006.01)
*A61B 5/00* (2006.01)
*A43B 7/14* (2006.01)
*A61B 5/11* (2006.01)
*A43B 13/14* (2006.01)
*A43B 17/00* (2006.01)
*A43B 13/02* (2006.01)

(52) U.S. Cl.
CPC .......... *A43B 7/1425* (2013.01); *A43B 7/1435* (2013.01); *A43B 13/14* (2013.01); *A61B 5/1038* (2013.01); *A61B 5/112* (2013.01); *A61B 5/6807* (2013.01); *A43B 13/00* (2013.01); *A43B 13/02* (2013.01); *A43B 17/00* (2013.01); *A61B 2562/0247* (2013.01); *A61B 2562/0252* (2013.01); *A61B 2562/125* (2013.01)

(58) Field of Classification Search
CPC ......... A43B 13/14; A43B 13/00; A43B 13/02; A43B 17/00; A61B 5/1038; A61B 5/112; A61B 5/6807; A61B 2562/0247; A61B 2562/0252; A61B 2562/125
USPC ....................................................... 36/25 R
See application file for complete search history.

(56) References Cited

U.S. PATENT DOCUMENTS

| | | | | |
|---|---|---|---|---|
| 6,216,545 B1* | 4/2001 | Taylor | ................. | A61B 5/1036 73/862.046 |
| 7,426,873 B1* | 9/2008 | Kholwadwala | .......... | A43B 3/00 73/777 |
| 7,726,206 B2* | 6/2010 | Terrafranca, Jr. | ..... | A43B 3/0005 73/862.041 |
| 8,467,979 B2* | 6/2013 | Sobolewski | ......... | A43B 1/0054 36/25 R |
| 9,089,182 B2* | 7/2015 | Schrock | ................. | A43B 3/00 |
| 9,357,947 B2* | 6/2016 | deGreef | ............... | A61B 5/1036 |
| 9,404,817 B2* | 8/2016 | Steier | ................... | A43B 3/0005 |
| 10,034,622 B1* | 7/2018 | Mahmoud | .............. | A61B 5/112 |
| 10,070,816 B2* | 9/2018 | Cowley | ................ | A61B 5/6807 |
| 10,159,427 B2* | 12/2018 | Malawey | .............. | A61B 5/1038 |
| 10,234,340 B2* | 3/2019 | Severinkangas | ........ | G01L 1/146 |
| 10,327,700 B2* | 6/2019 | Lee | ...................... | A61B 5/6807 |
| 10,478,095 B2* | 11/2019 | Agrawal | .............. | A61B 5/0022 |
| 2003/0097878 A1* | 5/2003 | Farringdon | .......... | A61B 5/1038 73/819 |
| 2010/0000121 A1* | 1/2010 | Brodie | ................. | A43B 3/0005 36/28 |
| 2011/0107771 A1* | 5/2011 | Crist | .................... | A43B 3/0005 62/3.3 |
| 2011/0199393 A1* | 8/2011 | Nurse | ...................... | A43B 3/00 345/665 |
| 2011/0230273 A1* | 9/2011 | Niegowski | ............. | A63B 24/00 473/199 |
| 2012/0109013 A1* | 5/2012 | Everett | ................ | A61B 5/1036 600/587 |
| 2015/0096203 A1* | 4/2015 | Brown | ................... | A43B 7/146 36/136 |
| 2016/0313174 A1* | 10/2016 | Lightstone | ............. | G01G 19/50 |
| 2016/0321947 A1* | 11/2016 | Toronto | ............... | A61B 5/0022 |
| 2016/0349076 A1* | 12/2016 | Campos Gallo | ..... | A43B 3/0005 |
| 2016/0375346 A1* | 12/2016 | Czaja | ................... | A63C 11/003 434/253 |
| 2017/0027512 A1* | 2/2017 | Yuan | .................. | A61B 5/02055 |
| 2017/0135417 A1* | 5/2017 | Lucrecio | .............. | A61B 5/1038 |
| 2017/0135606 A1* | 5/2017 | Hitchcock | ............ | A61B 5/1038 |
| 2017/0176266 A1 | 6/2017 | Matthieu et al. | | |
| 2018/0028862 A1* | 2/2018 | Statham | ............... | A61B 5/6895 |
| 2018/0055415 A1* | 3/2018 | Nakao | .................... | G16H 50/30 |
| 2018/0256071 A1* | 9/2018 | Mathieu | ............... | A43B 3/0005 |

* cited by examiner

SOLE OR INNER SOLE

The present invention relates to a sole or inner sole for a shoe, including a plurality of force sensitive resistors. The force sensitive resistors may be for use with stretchable materials.

Traditionally, force sensitive resistors are provided with a lower conductive member formed on a first substrate, and an upper conductive member formed on a second substrate. A spacer element is mounted between the first and second substrates. As the conductive members are moved toward and away from each other the resistance of the force sensitive resistor is altered. In this manner the force applied to the resistor can be determined by the change in the resistance. The substrates are required to be relatively stiff and resist stretching as otherwise the data from the force sensitive resistor will be corrupted.

This is particularly relevant as force sensitive resistors are often used in environments which receive significant forces and deformations. In particular, force sensitive resistors are being used in so-called "smart" clothing. This includes soles or inner soles for shoes which are used to generate data regarding the user's gait, pressure distribution and/or pronation.

Many existing shoes do not gather sufficient data of the correct points to measure all of these metrics. There is therefore a need to provide a sole or inner sole for a shoe which can provide suitable measurements to derive this information.

A sole or inner sole for a shoe is provided according to the present invention according to claim 1. The sole or inner sole comprising: a toe region for supporting a user's toes; a forefoot region for supporting a user's forefoot; a midfoot region for supporting a user's arch; a heel region for supporting a user's heel; a longitudinal direction extending from the heel region towards the toe region; a lateral direction transverse to the longitudinal direction extending from an inner side to an outer side of the sole or inner sole; a plurality of force sensors distributed throughout the sole or inner sole comprising: a first lateral row of force sensors in the toe region; a second lateral row of force sensors in the forefoot region; a first longitudinal row of force sensors along the inner side of the sole or inner sole from the heel region to the midfoot region; and a second longitudinal row of force sensors along the outer side of the sole or inner sole from the heel region to the midfoot region.

This sole or inner sole is provided with a higher density of force sensors, placed in the relevant locations, to allow high accuracy information regarding gait, weight distribution and pronation to be obtained.

Preferably, each row comprises at least three force sensors. More preferably, each row comprises at least four force sensors.

Preferably, most of the force sensors have the same shape. This reduces manufacturing costs and computational considerations for different outputs.

Preferably, most of the force sensors are substantially circular. More preferably, at least one of the force sensors is elongate compared to the other force sensors.

Preferably, the elongate sensor is provided in the first or second lateral row.

Preferably, the elongate sensor is the outermost sensor. This helps save space in smaller shoe sizes, and minimises data loss as the information relating to the outermost toes is the least relevant for analysis.

Preferably the sole or inner sole comprises an interior sealed region between the first and second longitudinal row.

The invention will now be described in detail, by way of example only, with reference to the accompanying drawings in which.

Figure 1:
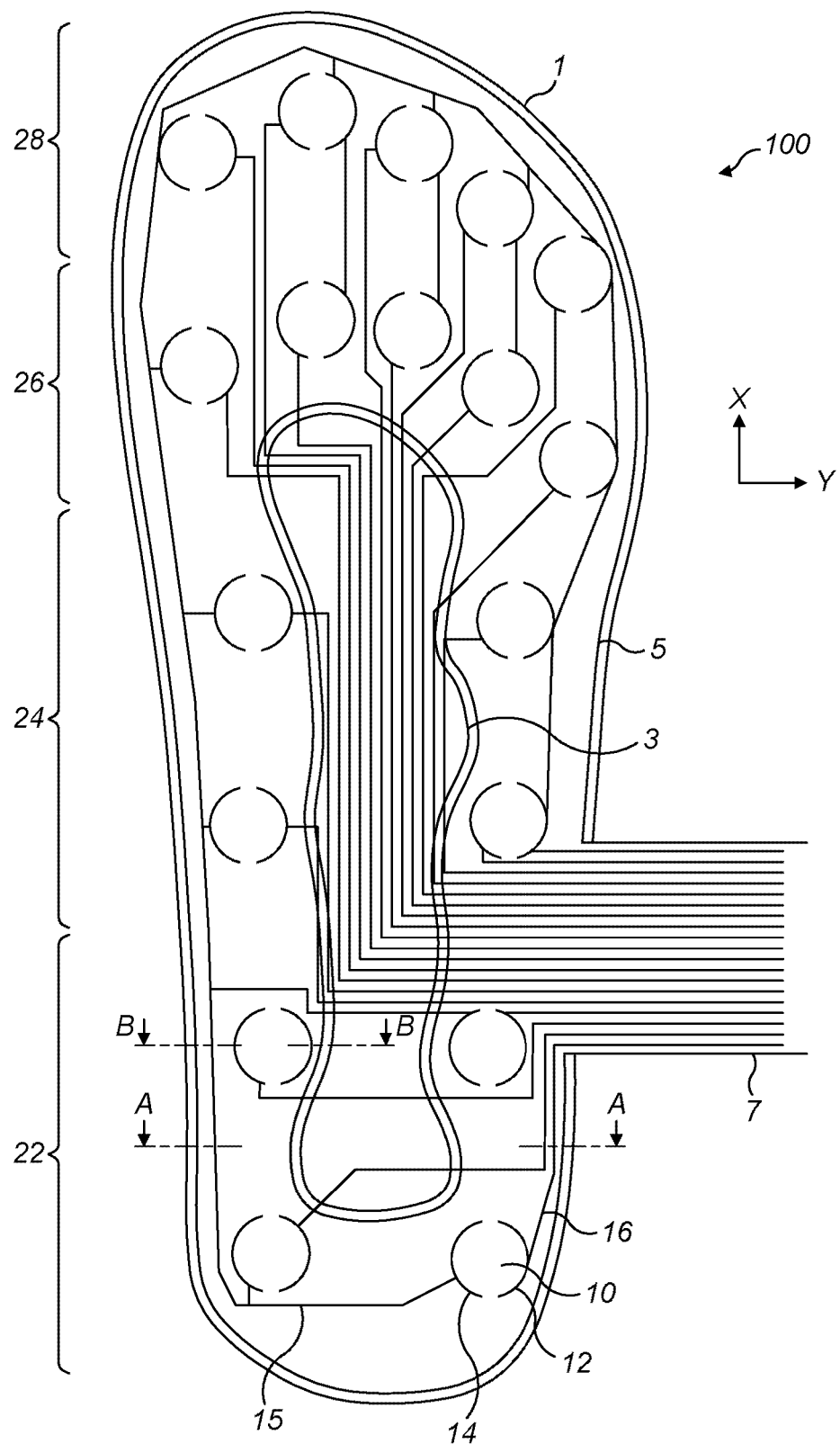
FIG. 1 is a top schematic view of a shoe insole comprising a number of force sensitive resistors according to the invention.

The sole (or insole/inner sole) 100 shown in FIG. 1 is formed of upper and lower flexible and stretchable layers 8, 9 (shown in FIG. 4) which are sealed in a water and air tight manner around their outer edge. While the term "sole" is used throughout the description, the described embodiment likewise may apply to an inner sole or insole. In particular, the layers 8, 9 may be sealed by means of heat or sonic welding. The sole 100 may be a separate, removable component, or may be integrated with a shoe. The sole 100 is shaped for a human foot and the embodiment of FIG. 1 defines two reference directions; a longitudinal direction X extending from a heel region 22 towards the back of the sole 100 to a toe region 28 towards the front of the sole 100, and a lateral direction Y extending from the inner side of the sole 100 corresponding to a medial side of a wearer's foot to the outer side of the sole 100 corresponding to a lateral side of the wearer's foot. While the sole shown in FIG. 1 is for a right foot, it is appreciated that a mirror version of this sole would be suitable for a left foot. Alternatively, the sole 100 may be usable for either foot by turning the sole 100 over.

Moving from the heel region 22 in the longitudinal direction, the sole 100 has a midfoot region 24, a forefoot region 26 and a toe region 28. In use, the heel region 22 supports the user's heel, the midfoot region 24 supports the user's arch, the forefoot region 26 supports the user's forefoot and the toe region 28 supports the user's toes.

Figure 2:
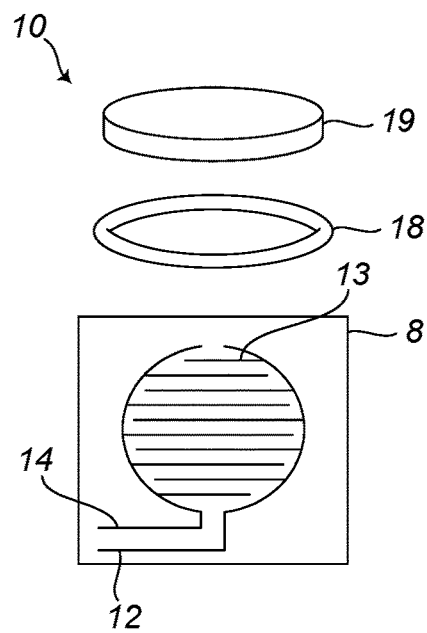
FIG. 2 is an exploded schematic, part plan, part perspective, view of a force sensitive resistor according to the invention.
Figure 3:
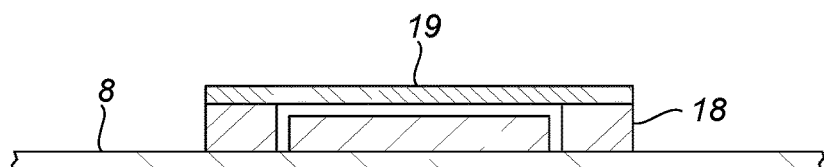
FIG. 3 is a side sectional view of the force sensitive resistor of FIG. 2.

The sole 100 is provided with a number of force sensitive resistors 10 arranged across the sole 100. An exemplary force sensitive resistor 10 is shown in FIG. 2. Conductive ink is printed on the bottom layer 8 in a pattern for a force sensitive resistor 10. This conductive ink forms electrodes 12, 14. These electrodes 12, 14 are substantially semi-circular with prongs 13 extending in alternating rows between the electrodes 12, 14. This forms a first conductive element. The prongs 13 have been omitted from the rest of the Figures for clarity, but they are present in each force sensitive resistor 10.

The bottom layer 8 is generally a small section of a larger sheet forming a larger structure. In particular, the bottom layer 8 may be a fabric, plastic or other flexible material which forms a part of a garment. While the present invention is generally described with respect to a sole 100, it is appreciated that it may be used with any other garment.

A garment is generally intended to mean anything which may be worn by a person. In particular, the garment may be any of a top, vest, trouser, jacket, helmet, inner sole, shoe, under-garment, or any other garment.

By printing the conductive ink onto this bottom layer 8 a force sensitive resistor 10 may be provided on the garment. The flexible bottom layer 8 may then contact a wearer and/or be subjected to an external impact force, and the force sensitive resistor 10 can determine the force applied by the wearer.

A spacer ring 18 is provided surrounding the first conductive element. A top sensor layer 19 is provided across the spacer ring 18. The top sensor layer 19 is flexible and comprises a second conductive element. Typically, the top sensor layer is formed from PET. The first and second conductive elements may be moved relative to one another in order to vary the resistance of the force sensitive resistor 10 as the user runs.

As the conductive ink is printed directly onto the stretchable lower layer 8, the output of the force sensitive resistor 10 may be altered when the lower layer 8 flexes and stretches and hence the results from the resistor 10 cannot be practically used. In order to address this, the upper sensor layer 19 is stiffer than the lower layer 8. This provides the localised region of the lower layer 8 with enhanced strength, on which the first conductive element is printed. In particular, this is achieved by the upper sensor layer 19 having a higher Young's modulus than the lower layer 8. This locally limits the ease of stretching of the lower layer 8 in the region of the first conductive element within the spacer 18. As such, the first conductive element may be printed directly on to the lower flexible layer 8 whilst still obtaining useful data.

As shown in FIG. 1, the lower layer 8 is provided with printed conductive tracks connected to the electrodes 12, 14 of the force sensitive resistor 10. As shown, there may be a single ground track 15 to which each force sensitive resistor 10 is connected. This reduces the space required for the tracks. Each force sensitive resistor 10 is also provided with its own data track 16. The sole is provided with a tab 7 which provides a pathway for the conductive tracks 15, 16 to an external CPU and control system (not shown). The tab 7 is integral with the bottom layer 8 and is likewise flexible and stretchable. While the present figures are shown with an external CPU and control system, this is not necessarily the case, and the CPU and control system may be integral with the sole 100 or provided in another layer designed to be contained within the shoe with the sole 100.

The upper and lower flexible layers 8, 9 of the sole 100 are also sealed in a water and air tight manner across a portion of the central region of the sole 100. This forms a central sealed region 3 on the sole which may extend across the heel region 22, the midfoot region 24 and the forefoot region 26.

Figure 4:
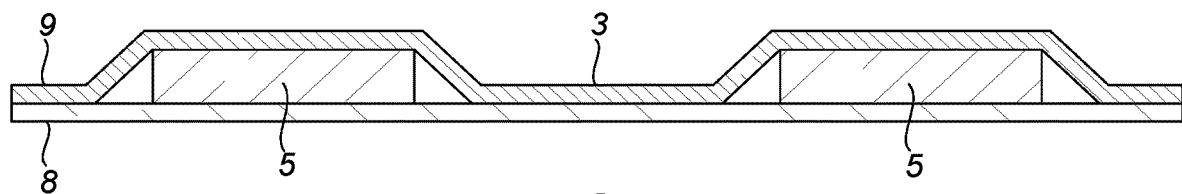
FIG. 4 is a sectional view along the line A-A of FIG. 1.

As shown in FIG. 4, which is a schematic view along A-A as shown on FIG. 1. Between the outer seal and the central sealed region 3, a compressible material 5 is provided. The compressible material 5 is designed to not seal to either of the upper and lower flexible layers 8, 9. In particular the layers 8, 9 should not sonic weld to the compressible material 5. The compressible material 5 is free between the upper and lower flexible layers 8, 9. In particular, the upper and lower flexible layers 8, 9 are not bonded to the compressible material 5. This leaves the compressible material 5 free to move in the gap between the layers 8, 9. As the compressible material 5 is substantially continuous, it is held in position by the central sealed region 3 as shown in FIG. 1.

Figure 5:
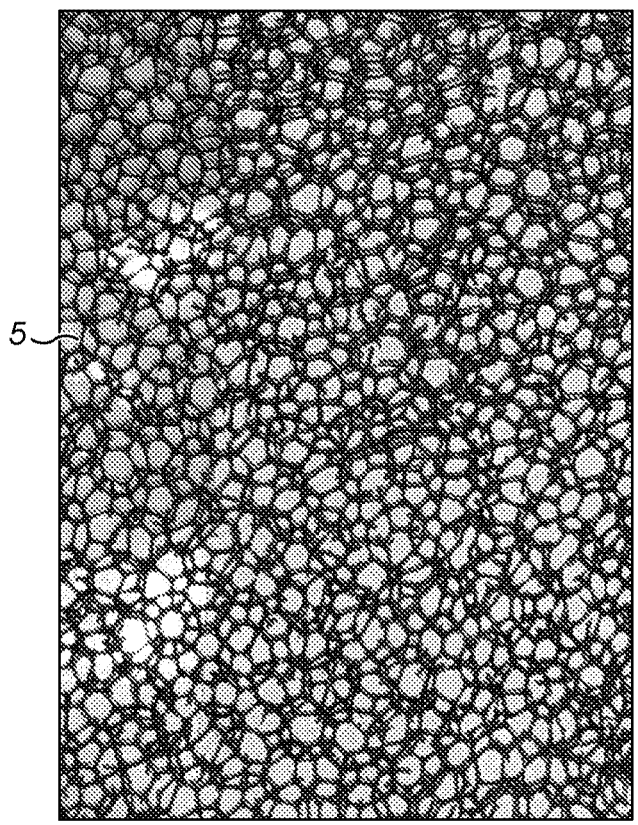
FIG. 5 is a view of a cushioning material for use in the sole of FIG. 1.

The compressible material may be any suitable material. In particular embodiments it is a foam material, with either an open cell or closed cell arrangement. FIG. 5 shows an exemplary open cell foam which may be used with the present invention. High resilience to deformation is necessary to ensure that the sole 100 is not permanently deformed in use. The material 5 may form the main support material of the sole 100, or an additional cushioning material may also be provided for enhanced comfort. The material 5 is selected to have a higher melting point than the material of the first and second layers 8, 9 such that the layers 8, 9 will seal to one another around the material 5 without sealing to the material 5.

The material 5 may be provided across multiple force sensitive resistors 10. That is, the material 5 may be shared by a plurality of force sensitive resistors 10.

Figure 6:
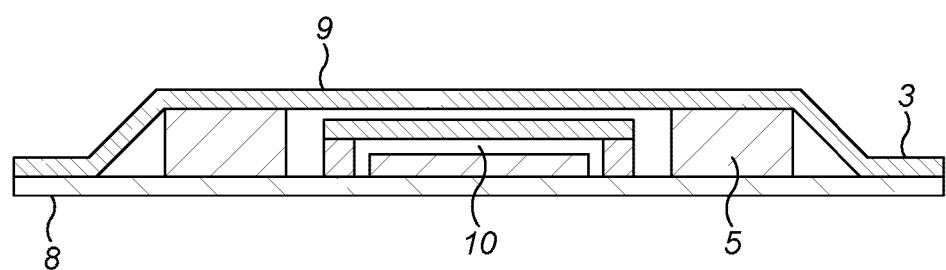
FIG. 6 is a sectional view along the line B-B of FIG. 1.

As shown in FIG. 6 which is a sectional view along B-B, in preferred embodiments the material 5 is provided with cutaway sections substantially aligned with the force sensitive resistors 10. In particular, these cut-away sections may be formed such that the material 5 substantially surrounds the force sensitive resistor 10. The material 5 may then not have any overlap with the force sensitive resistor 10.

Figure 7:
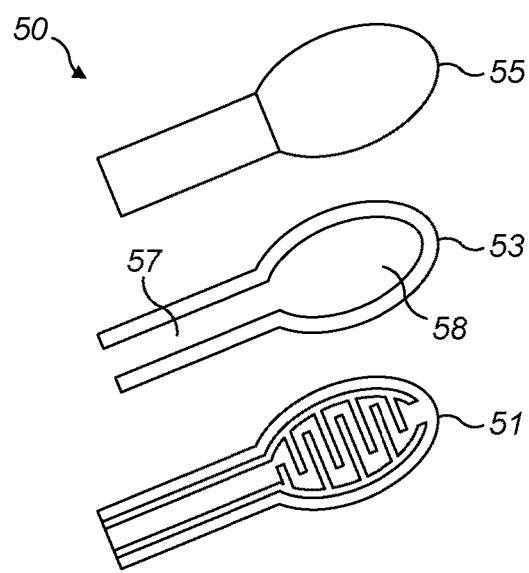
FIG. 7 is an exploded schematic view of a force sensitive resistor according to the prior art.

Air is able to flow through the material 5. This allows the entirety of the sole 100 to be sealed around its outer edge. Typically, prior art force sensitive resistors 50 as shown in FIG. 7 which are formed of first conductive element 51, spacer 53 and second conductive element 55. The spacer 53 is provided with a vent pathway 57 extending from the spacer chamber 58 extending from the spacer chamber 58. The spacer chamber 58 is provided between the conductive elements.

As the conductive elements are moved towards and away from one another, the volume of the spacer chamber 58 is varied. Accordingly, air which is held in the spacer chamber 58 must be expelled via the vent pathway 57 otherwise the prior art force sensitive resistor 50 may rupture. As such, in prior art soles without the air permeable compressive material 5 of the present invention, a vent pathway must be provided from the force sensitive resistor 50 to the atmosphere outside of the sole 100. While efforts are made to minimise these vent pathways, they represent pathways via which moisture may ingress and damage the sole 100.

By providing the air permeable material 5, these vent pathways are no longer necessary. The air displaced by movement of the force sensitive resistors 10 can be distributed across the sole 100 without risking rupture. This allows the entire sole 100 to be sealed to the atmosphere, which ensures better moisture resistance than known systems.

Figure 9:
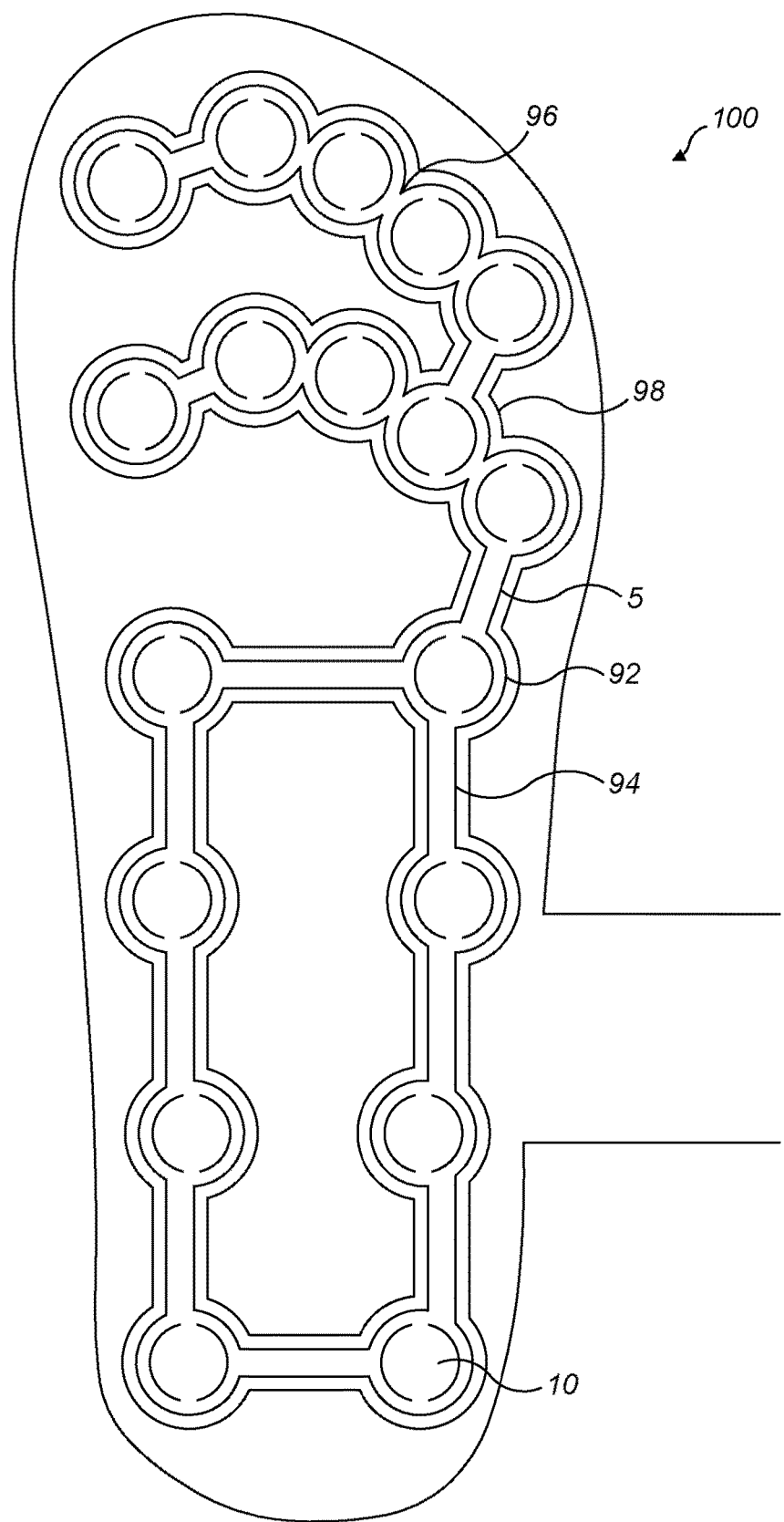
FIG. 9 is a top schematic view of an alternative shoe insole comprising a number of force sensitive resistors according to the invention.

FIG. 9 shows an alternative embodiment of a sole 1. The wiring of the earlier embodiments is not shown in from this Figure for ease of understanding. The wiring of this embodiment is substantially the same as described with the other embodiments. In this embodiment, the compressible material 5 does extend generally across the sole but instead is concentrated in regions around the force sensitive resistors 10 in circular regions 92 surrounding each force sensitive resistor. As the compressible material 5 has a higher melting point than the material of the sole, a seal 98 will be formed around the shape of the compressible material 5.

In the embodiment of FIG. 9, connecting portions 94 of compressible material 5 join the circular sections 92 to form a continuous region of compressible material 5. In the toe and forefoot regions 28, 26 the circular sections 92 may have some degree of overlap 96.

In the embodiment shown in FIG. 9, the compressible material 5 is continuous across all of the force sensitive resistors. However, this is not necessarily the case. In other embodiments particular regions may each have their own discrete regions of compressible material 5. For example, there may be one discrete region in the toe region 28, one discrete region in the forefoot region 26 and two discrete regions down either side of the sole in the heel and midfoot regions 22, 24. Alternatively, each force sensitive resistor 10 may have its own discrete sealed section of compressible material 5. There may also be a combination of individual discrete sealed sections and discrete regions of compressible material 5. For example, the toe and forefoot regions 28, 26 may each have their own discrete region of compressible material 5, while the force sensitive resistors 10 in the heel and midfoot regions 22, 24 may be in individual discrete sealed sections of compressible material.

The force sensitive resistors 10 are distributed throughout the sole 100. This ensures that a detailed understanding of the user's weight distribution can be calculated, along with information such as the degree of pronation of the user while walking. In particular, as shown in FIG. 1, each region 22, 24, 26, 28 comprises an individual sensing area comprising a plurality of force sensitive resistors 10. These force sensitive resistors 10 are generally similar in shape to one another, in that they are each substantially circular. In each of the toe and forefoot regions 28, 26 a row of force sensitive resistors 10 extending laterally Y across the sole 100 are provided. In particular, each row comprises five force sensitive resistors arranged to acquire data regarding each toe and corresponding toe knuckle.

Figure 8:
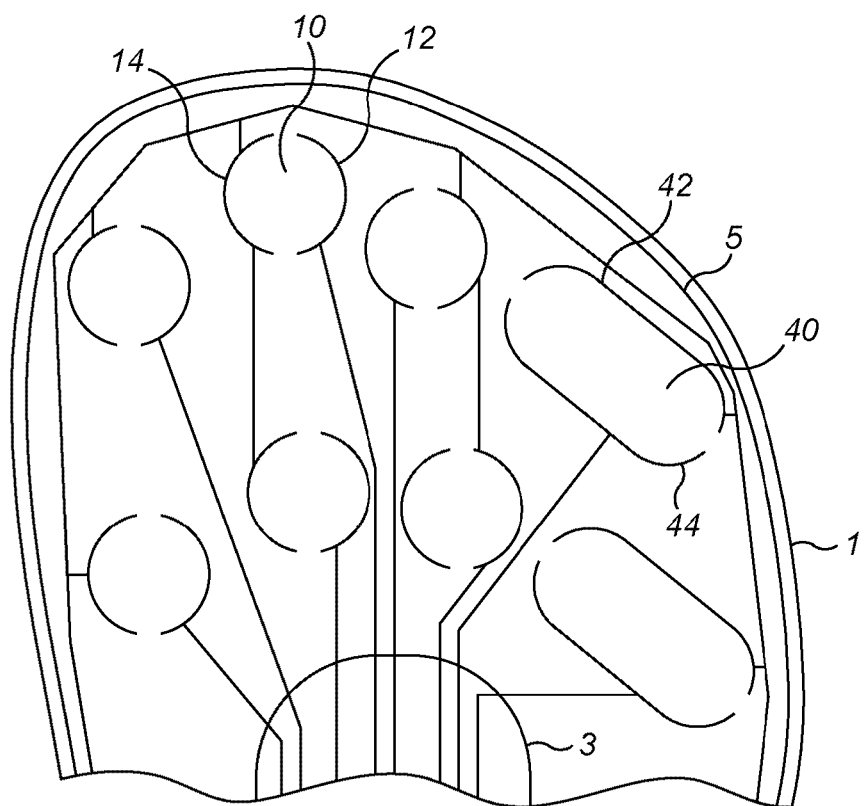
FIG. 8 is a top schematic view of a shoe insole comprising a number of force sensitive resistors according to a further embodiment of the invention.

While this arrangement in the toe and forefoot regions 28, 26 is ideal it may not be possible in all embodiments. In particular, for soles 100 designed for smaller feet it may not be possible to fit five separate force sensitive resistors 10 across the lateral direction Y. Accordingly, an arrangement such as that shown in FIG. 8 may be provided. As shown, the innermost three force sensitive resistors 10 are provided as in FIG. 1. However, instead of two separate outer force sensitive resistors 10, a single force sensitive resistor 40 is provided. This force sensitive resistor 40 is elongated in the lateral direction Y to cover the outer part of the toe and forefoot regions 28, 26. This elongated force sensitive resistor 40 is substantially rectangular with rounded ends in FIG. 8. However, any suitable shape may be used. The force sensitive resistor 40 is provided with electrodes 42, 44 and functions as the circular force sensitive resistors 10 described above. It has been identified that the data from the individual outer toes is not of as much interest as the inner regions. Accordingly, the data from the outermost toes can be combined while still being useful for analytics.

Across the heel and midfoot regions 22, 24 two longitudinal rows of force sensitive resistors 10 are provided. One row is on the inner side of the sole and the other row is on the outer side, with the sealed central region 3 provided between these rows. At least one force sensitive resistor 10 is provided in each row in each of the heel and midfoot regions 22, 24. Preferably, if the sole 100 is big enough, each row has two force sensitive resistors 10 in each of the heel and midfoot regions 22, 24.

By providing force sensitive resistors 10 in this arrangement a high quality of data can be obtained that provides a lot of information regarding the weight distribution and pronation of the user.

The invention claimed is:

1. A sole or inner sole for a shoe comprising:
a toe region for supporting a user's toes;
a forefoot region for supporting a user's forefoot;
a midfoot region for supporting a user's arch;
a heel region for supporting a user's heel;
a longitudinal direction extending from the heel region towards the toe region;
a lateral direction transverse to the longitudinal direction extending from an inner side of the sole or inner sole to an outer side of the sole or inner sole opposite of the inner side, the inner side of the sole or inner sole corresponding to a medial side of a wearer's foot and the outer side of the sole or inner sole corresponding to a lateral side of the wearer's foot when the sole or inner sole is worn;
a plurality of force sensors distributed throughout the sole or inner sole comprising:
a first lateral row of force sensors in the toe region,
a second lateral row of force sensors in the forefoot region,
a first longitudinal row of force sensors positioned along the inner side of the sole or inner sole in the longitudinal direction from the heel region to the midfoot region, and
a second longitudinal row of force sensors positioned along the outer side of the sole or inner sole in the longitudinal direction from the heel region to the midfoot region;
an interior sealed region formed by an upper flexible layer and a lower flexible layer sealed together in a central region of the sole or inner sole, where the interior sealed region is positioned between the first and second longitudinal row of force sensors; and
a compressible material positioned between the upper flexible layer and the lower flexible layer, the compressible material including cutaway sections in which the plurality of force sensors are deposited;
wherein the upper flexible layer and the lower flexible layer are sealed together around the outer edge of the sole or inner sole to form an outer seal, and the compressible material is positioned between the outer seal and the interior sealed region.

2. The sole or inner sole for the shoe according to claim 1, wherein each row comprises at least three force sensors.

3. The sole or inner sole for the shoe according to claim 2, wherein each row comprises at least four force sensors.

4. The sole or inner sole for the shoe according to claim 1, wherein at least half of all the force sensors have the same shape.

5. The sole or inner sole for the shoe according to claim 4, wherein at least half of all the force sensors are circular.

6. The sole or inner sole for the shoe according to claim 4, wherein at least one of the force sensors is elongated.

7. The sole or inner sole for the shoe according to claim 6, wherein the elongated sensor is provided in the first or second lateral row.

8. The sole or inner sole for the shoe according to claim 6, wherein the elongated sensor is the outermost sensor.

9. The sole or inner sole for the shoe according to claim 1, wherein the interior sealed region is watertight and airtight.

* * * * *